United States Patent [19]

Minatelli et al.

[11] Patent Number: 4,503,230

[45] Date of Patent: Mar. 5, 1985

[54] ALKYLATION OF SUBSTITUTED SULFONYLPYRIDINES

[75] Inventors: John A. Minatelli, Watertown; Shih-Yu Ma, Cheshire, both of Conn.

[73] Assignee: Uniroyal, Inc., Middlebury, Conn.

[21] Appl. No.: 294,665

[22] Filed: Aug. 20, 1981

[51] Int. Cl.³ ............................................ C07D 213/62
[52] U.S. Cl. ..................................... 546/294; 546/275
[58] Field of Search .................................. 546/294, 295

[56] References Cited

U.S. PATENT DOCUMENTS 3,668,255 6/1972 Meuly et al. ........................ 568/393

OTHER PUBLICATIONS

Golinski et al., Synthesis, 1979, pp. 461–462.
Takahata et al., Heterocycles, vol. 12, No. 11, 1979.
Dehmlow et al., Phase Transfer Catalysis, p. 116, Verlag Chemi., 1980.

Primary Examiner—Jane T. Fan
Attorney, Agent, or Firm—John A. Shedden

[57] ABSTRACT

A process for making a compound of the formula

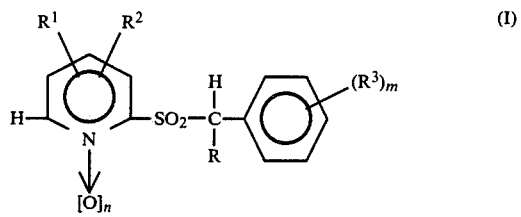

is disclosed wherein:

R is $C_1$-$C_{12}$ alkyl, allyl or benzyl, $R^1$ and $R^2$ are hydrogen, halogen, $C_1$-$C_4$ alkyl, or phenyl, $R^3$ is hydrogen, halogen, $C_1$-$C_4$ alkyl, $C_1$-$C_4$ alkoxy, $CF_3$, $NO_2$, phenyl or phenoxy, m is an integer from 1 to 3 and n is zero or 1, by contacting a compound of said formula where R is hydrogen with certain halohydrocarbons in the presence of solid KOH, a phase transfer catalyst, a solvent and an effective amount of water. The process of this invention permits production of the above compound, useful as a herbicide, without the need for cocatalysts or excess high concentration of NaOH and water.

12 Claims, No Drawings

ALKYLATION OF SUBSTITUTED SULFONYLPYRIDINES

This invention relates to a process for alkylation of substituted sulfonylpyridine 1-oxides, useful for example as herbicides.

More particularly, the invention is concerned with a process for making a compound having the structural formula

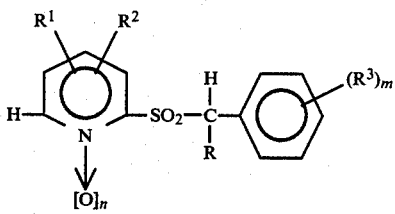
(I)

wherein:
R is $C_1$-$C_{12}$ alkyl (e.g., methyl, ethyl, t-butyl, iso-octyl, dodecyl), allyl or benzyl;
$R^1$ and $R^2$ are hydrogen, halogen, $C_1$-$C_4$ alkyl (e.g., methyl, ethyl, n-butyl, t-butyl), or phenyl;
$R^3$ is hydrogen, halogen (fluorine, chlorine, bromine or iodine), $C_1$-$C_4$ alkyl (e.g., methyl, butyl), $C_1$-$C_4$ alkoxy (e.g., methoxy, propoxy), phenyl, phenoxy, $CF_3$ or $NO_2$; n is zero or 1; and m is an integer from 1 to 3, and if m is greater than 1, the $R^3$s may be the same or different;
by reacting a compound having the structural formula

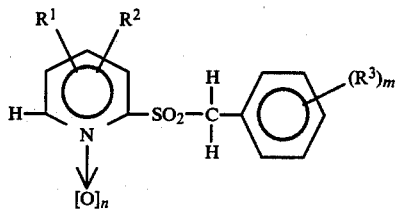
(II)

wherein $R^1$, $R^2$, $R^3$, n and m have the meanings expressed above, with an alkylating agent having the structural formula

XR   (III)

wherein X is chlorine or bromine and R is as defined above;
in the presence of
(a) a quaternary ammonium or phosphonium salt,
(b) solid KOH and NaOH at a molar KOH/NaOH ratio of from 25/75 to 100/0,
(c) an effective amount of water, and
(d) a solvent inert toward the reactants.

In one aspect, the invention is directed to a process by which a substituted sulfonylpyridine 1-oxide of formula (II) such as 2-[(2,5-dimethylphenyl)methylsulfonyl]-pyridine 1-oxide can be successfully alkylated to products of formula (I) such as 2-[1-(2,5-dimethylphenyl)ethylsulfonyl]pyridine 1-oxide using a phase transfer catalyst (PTC) employing solid KOH, with or without NaOH present.

M. Makosza et al. Synthesis 461 (1979), describe a reaction in which various aryl alkyl sulfones in the presence of $CH_2Cl_2$, alkylhalide, 50% aqueous NaOH and a phase transfer catalyst, are alkylated in the position adjacent to the sulfonyl group. They noted that addition of small amounts of hexamethyl phosphoric triamide accelerated the reaction considerably. We have found that 2-[(2,5-dimethylphenyl)methylsulfonyl]pyridine 1-oxide undergoes alkylation smoothly with 50% aqueous NaOH at 40° C. under conditions described by Makosza et al. with the exception that hexamethylphosphoric triamide is not required to achieve satisfactory results. This reaction is not commercially feasible because a large excess of 50% NaOH is needed for taking up the water formed during the reaction and, yet, maintaining a very high concentration of NaOH. This is a critical factor peculiar to PTC mediated alkylations. It is undesirable to handle such large amounts of caustic solution (typically 11.5:1 molar ratio of NaOH to 2-[(2,5-dimethylphenyl)methylsulfonyl]-pyridine 1-oxide are required) in order to obtain 2-[1-(2,5-dimethylphenyl)ethylsulfonyl]pyridine 1-oxide.

U.S. Pat. No. 3,668,255, June 6, 1972, Meuly et al., describes the carbon alkylation of ketones using solid KOH or NaOH in the presence of an organic amine and/or ammonia catalyst. No quaternary amines are mentioned in this process. It is known that nonquaternized amines of themselves do not catalyze such reactions.

Takahata et al. Heterocycles 12 (11), 1449 (1979) describes a nitrogen alkylation of lactams involving pulverized KOH in tetrahydrofuran and in the presence of tetrabutylammonium bromide.

The invention is based on the discovery that substituted sulfonyl pyridine 1-oxides of formula (II) may be readily alkylated with compounds of formula (III) to yield compounds of formula (I) in the presence of only about a one molar excess of solid KOH (such as 90 to 92% flake) and about 10 to 12% water all based on compound (II) and in the presence of a phase transfer catalyst. The reaction may be carried out in a relatively short time and it produces a good yield at high purity. It is interesting to note that the yields are unsatisfactory with solid NaOH alone at the same molar rate as KOH. The solvents employed are inexpensive and quite easily recovered. In addition, wet starting compound (II) can be used. As a matter of fact such wet (II) may provide the effective amount of water necessary for the reaction to proceed.

Compounds of the formula I which may be prepared in accordance with the invention include 2-[1-(2,5-dimethylphenyl)ethylsulfonyl]-5-bromopyridine 1-oxide, 2-(1-phenylpropylsulfonyl)-4-chloropyridine 1-oxide, 2-[1-(2-ethyl-4-methoxyphenyl)butylsulfonyl]-3-methyl-4-t-butylpyridine 1-oxide, 2-[1-(2-isopropoxy-4-t-butylphenyl)hexylsulfonyl]-3,4-dipropylpyridine 1-oxide, 2-[1-(2-methyl-3-butoxyphenyl)nonylsulfonyl]-pyridine, 2-[1-(2-ethyl-5-fluorophenyl)tridecylsulfonyl]-4,5-dimethylpyridine 1-oxide, 2-[1-(5-nitrophenyl)buten-3-ylsulfonyl]pyridine 1-oxide, 2-[1-(2-chloro-4-bromophenyl)phenethylsulfonyl]-3-methylpyridine 1-oxide, 2-(1-biphenylheptylsulfonyl)pyridine 1-oxide, 2-[1-(2-chloro-5-trifluoromethylphenyl)ethylsulfonyl]pyridine 1-oxide and the like.

Alkylating reagents of the formula (III) which may be used to prepare such compounds from starting materials of formula II include methyl chloride, ethyl bromide, propyl bromide, n-butyl chloride, t-butyl bromide, amyl chloride, octyl bromide, decyl chloride, dodecyl chloride, allyl chloride, benzyl bromide, etc.

As indicated, the process of the invention is typically carried out in the presence of
(a) a quaternary ammonium or phosphonium salt,
(b) solid KOH and NaOH at a molar KOH/NaOH ratio of from 25/75 to 100/0,
(c) an effective amount of water, and
(d) a solvent inert towards the ingredients.

Typical PTC's which may be used in the invention include benzyltriethylammonium bromide, benzyltrimethylammonium chloride, benzyltributylammonium chloride, benzyltripropylammonium chloride, methyltributylammonium chloride, methyltributylammonium bromide, tetrabutylammonium hydrogen sulfate, tetrabutylammonium chloride or bromide, cetyltrimetylammonium bromide, tetrabutylammonium hydroxide, benzyltriethylammonium hydroxide, tetrabutylphosphonium chloride or bromide, benzyltributylphosphonium chloride or bromide, methyltriethylphosphonium bromide or chloride and the like (see also Starks, JACS 93, 195 (1971)).

Inert solvents that may be used in the process of the invention include methylene chloride, tetrahydrofuran dimethylformamide and dioxane.

The concentration of starting compound (II) in the reaction solution is almost invariably within the range of from 5 g or less to 50 g or more per 100 ml of solvent, but other concentrations may be used. A concentration of 10 g to 40 g is preferred, more preferably it is from 21 to 30 g of (II) per 100 ml of solvent.

Reaction conditions may be varied over a wide range as desired. The following tabulation may serve as a guide.

| | Reaction Conditions | | |
|---|---|---|---|
| | Broad | Preferred | Most Preferred |
| Temperature, °C. | 0–40 | 10–30 | 10–30 |
| Pressure, psi (kPa) | 0–15 (0–105) | 0–12 (0–85) | 0–10 (0–70) |
| Time, hrs | 2–12 | 3–8 | 4–6 |

Other conditions may be used if desired.

After the reaction, an organic layer is usually separated and washed (e.g. with water, dilute hydrochloric acid, or the like). The solvent may be at least partially removed by conventional means; addition of a non-solvent (e.g., hexane or heptane) precipitates the product, which can be recovered by means of centrifuging, filtering or the like.

Yields are remarkably high (e.g., 85% or even more based on the starting material (II)), and the product has exceptional purity (ordinarily over 95%).

The process is energy efficient and has a low requirement of raw material (particularly caustic). Not only are short reaction/process times made possible, but an added convenience is that the starting material (II) can be employed as a wet cake, with no need for preliminary drying. The inexpensive solvents that may be used add to the economy of the process, and the results are particularly satisfactory from the standpoint of the purity of the final product.

In a preferred practice of the invention the molar II/III ratio is from 1/1 to 1/10; the molar II/KOH plus NaOH ratio is from ½ to 1/5 and the molar II/quaternary salt ratio is from 99/1 to 90/10, and II and III are at least partially soluble in the solvent.

Particularly useful are molar II/H$_2$O ratios of from 92/8 to 80/20 not taking into account the about 6 to 10 percent of water associated with solid, highly concentrated KOH (85–92% based on K$_2$O).

A preferred concentration of II is from 5 to 40 g per 100 ml of solvent.

In one aspect the invention is directed to a process in which the quaternary salt is separately prepared before addition to the reactor.

In another form of the invention the quaternary salt is formed in situ (e.g., addition of a tertiary amine to excess alkyl halide produces the PT catalyst in situ).

On a large scale the presence of 6 to 20 mole percent of water per mole of compound (II) is critical to ensure that the process proceeds reliably.

Thus, when the reagents, the PTC, etc. are mixed in a closed reaction flask, there is instantly formed a deep red color followed by an exotherm (up to 45°–50° C.). The reagents employed in this process frequently contain low-boiling point materials e.g., methyl chloride b.p. −24° C., methylene chloride b.p. +40° C. The sudden temperature increase could result in an undesirable pressure surge. The addition of water appears to initiate and moderate the process at such a rate that no sudden temperature increase will take place.

Furthermore, it has been discovered, in accordance with the invention, that the PTC alkylation of (II) is unpredictable without the presence of water. Experimental evidence indicates that the reaction does not proceed without a sufficient amount of water present.

The following examples will serve to illustrate the practice of the invention in more detail.

EXAMPLE 1

In a 2-liter resin reaction flask equipped with water cooling jacket, thermometer, mechanical stirrer, addition funnel and a 7.5 p.s.i. safety valve, were placed 108 g of KOH (90%, flake) and 240 g of 2-[(2,5-dimethylphenyl)methylsulfonyl]pyridine 1-oxide.

In a separate flask, 750 ml of methylene chloride were cooled with an ice-water bath, and 87.6 g of methyl chloride were introduced. The methylene chloride solution of methyl chloride was poured into the reaction flask followed by the addition of 1.8 ml of water. The reaction mixture was stirred and followed by the slow addition of a solution of 9.6 g (5 mole%) of benzyltriethylammonium chloride in 50 ml of methylene chloride over a period of 20–30 minutes.

The reaction temperature gradually increased from 16° C. to 25° C. Twenty or thirty minutes after the addition, the reaction temperature began to drop. The water cooling was turned off. Then, the temperature gradually increased again and peaked at approximately 29° C. Three hours after the addition of benzyltriethylammonium chloride, the reaction was completed.

The dark brown mixture was transferred to a separatory funnel and washed with 800 ml of water. The lower organic layer was separated. It was further washed with 800 ml of water plus 40 ml of 6N HCl and thereafter with 800 ml of water The methylene chloride solution was filtered to remove any insoluble impurities, followed by concentration and addition of 1.0 liter of n-heptane to precipitate the alkylated product. The off-white product was collected by filtration, dried in an oven (90° C.); it weighed 236 g (93.8%); m.p. 156°–160° C., HPLC analysis:
Alkylated product: 92.4%
Starting material: Trace

EXAMPLE 2

Following the reaction conditions of Example 1, with the exception that one mole of KOH is used per mole of (II), gave after the usual time and workup, a reaction product whose NMR showed approximately 50% (II) and 50% (I). This indicated that at least two mole equivalents of base are needed to complete the reaction.

EXAMPLE 3

Example 1 was essentially repeated except that as base a mixture of solid KOH (90% flake) and solid NaOH (98.6%) at a molar ratio of 1/1 was used; the molar ratio of KOH plus NaOH to 2-[(2,5-dimethylphenyl)methylsulfonyl]pyridine 1-oxide was 2 to 1. The reaction period was about 4 hours, and the temperature was kept between 15° and 31° C. Product yield was 92.3% 2-[1-(2,5-dimethylphenyl)ethylsulfonyl]pyridine 1-oxide.

EXAMPLE 4

To a 100 ml round bottom, 3-necked flask equipped with thermometer, stirrer, were charged 0.5 g (3.2 mmoles) 2-(phenylmethylsulfonyl)-4-methylpyridine 1-oxide, 10 ml CH$_2$Cl$_2$, 0.05 g benzyltriethylammonium chloride and 0.75 ml n-butyl bromide. Said mixture also contained about 5 mg (0.28 mmoles) of water. Immediately, a dark red color formed while the reaction mixture was kept at about 15° while stirring. With time, the color faded, and after 3 hours reaction time, the product (2-(1-phenylpentylsulfonyl)-4-methylpyridine 1-oxide) was isolated, having a melting range of 120°–122° C. The product structure was confirmed by NMR and IR analysis.

EXAMPLE 5

Example 4 was repeated except instead of butyl bromide, 1-chlorobutane was used, and instead of benzyltriethylammonium chloride, 0.041 g of tri-n-butylamine was employed. The resultant reaction mixture developed a dark red color and after 3 hours reaction time at about the same temperature range, the product (2-(1-phenylpentylsulfonyl)-4-methylpyridine 1-oxide was isolated. Yield 92.9%.

EXAMPLE 6

3.2 mmoles of 2-[(4-chlorophenyl)methylsulfonyl]-4-bromopyridine was contacted with 7.0 mmoles bromoethane using essentially the conditions of Example 4 providing about 93% yield of 2-[1-(4-chlorophenyl)propylsulfonyl]-4-bromopyridine.

EXAMPLE 7

Example 6 was repeated except that 2-[4-bromophenyl)methylsulfonyl]pyridine 1-oxide and 1-chloropropane were used as starting materials yielding 2-[1-(4-(bromophenyl)butylsulfonyl]pyridine 1-oxide of high purity.

What is claimed is:

1. A process for making a substituted sulfonylpyridines of the formula

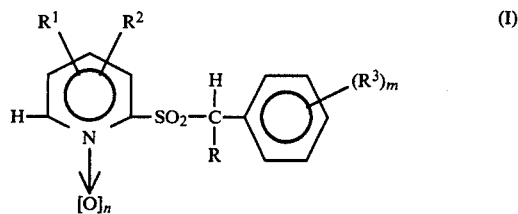

wherein R is C$_1$-C$_{12}$ alkyl, allyl or benzyl;
R$^1$ and R$^2$ are hydrogen, halogen, C$_1$-C$_4$ alkyl or phenyl;
R$^3$ is hydrogen, halogen, C$_1$-C$_4$ alkyl, C$_1$-C$_4$ alkoxy, phenoxy, CF$_3$, NO$_2$ or phenyl; and
n is 0 or 1, and m is an integer from 1 to 3; comprising contacting a compound having the structural formula

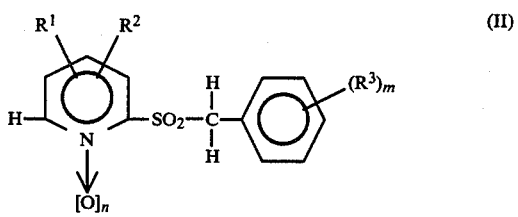

wherein R$^1$, R$^2$, R$^3$, n and m have the meanings expressed above, with an alkylating agent having the structural formula

XR    (III)

wherein X is chlorine or bromine and R has the meanings above;
in the presence of
(a) a quaternary ammonium or phosphonium salt,
(b) solid KOH and NaOH at a molar KOH/NaOH ratio of from 25/75 to 100/0, said KOH and NaOH together present in a concentration such that their molar ratio to said compound II is in the range of 2:1 to 5:1,
(c) water present in a concentration such that the molar ratio of compound II to water is in the range of from 92/8 to 80/20, and
(d) a solvent inert toward the reactant; and subjecting the mixture to alkylating reaction conditions.
2. The process of claim 1 wherein the molar II/III ratio is from 1/1 to 1/10; the molar II/quaternary salt ratio is from 99/1 to 90/10; and II and III are at least partially soluble in said solvent.
3. The process of claim 1 wherein the concentration of II is from 5 to 40 g per 100 ml of solvent.
4. The process of claim 1 wherein the quarternary salt is added per se to the reaction mixture.
5. The process of claim 1 wherein the quaternary salt is formed in situ in the reaction mixture.
6. The process of claim 1 wherein (III) is CH$_3$Cl, n-butylbromide or n-butyl chloride.
7. The process of claim 1 wherein (I) is 2-[1-(2,5-dimethylphenyl)ethylsulfonyl]pyridine 1-oxide and (II) is 2-[(2,5-dimethylphenyl)methylsulfonyl]pyridine 1-oxide.
8. The process of claim 6 wherein (a) is benzyltriethylammonium chloride, tetrabutylammonium chloride, tetrabutylammonium bromide, or tetrabutyl ammonium hydroxide.
9. The process of claim 6 wherein (d) is methylene chloride.
10. The process of claim 1 wherein R$^1$, R$^2$ and R$^3$ are hydrogen, bromine, chlorine or C$_1$-C$_4$ alkyl, and m is 1 or 2.
11. The process of claim 1 wherein said reaction of compound II with compound III occurs in the absence of a cocatalyst.
12. The process according to claim 1 wherein the overall KOH/H$_2$O weight ratio is from 84.7:15.3 to 90.6:9.4.

* * * * *